US 11,809,625 B2

(12) United States Patent
Halgand et al.

(10) Patent No.: US 11,809,625 B2
(45) Date of Patent: Nov. 7, 2023

(54) METHOD FOR CONTROLLING A LIMB OF A VIRTUAL AVATAR BY MEANS OF THE MYOELECTRIC ACTIVITIES OF A LIMB OF AN INDIVIDUAL AND SYSTEM THEREOF

(71) Applicants: UNIVERSITÉ DE BORDEAUX, Bordeaux (FR); CENTRE NATIONAL DE LA RECHERCHE SCIENTIFIQUE, Paris (FR)

(72) Inventors: Christophe Halgand, Saint André de Cubzac (FR); Matthieu Guemann, Bordeaux (FR); Aymar Goullet De Rugy, Bordeaux (FR); Daniel Cattaert, Gujan-Mestras (FR)

(73) Assignees: UNIVERSITÉ DE BORDEAUX, Bordeaux (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 0 days.

(21) Appl. No.: 17/910,963

(22) PCT Filed: Mar. 12, 2021

(86) PCT No.: PCT/EP2021/056373
§ 371 (c)(1),
(2) Date: Sep. 12, 2022

(87) PCT Pub. No.: WO2021/180945
PCT Pub. Date: Sep. 16, 2021

(65) Prior Publication Data
US 2023/0147243 A1    May 11, 2023

(30) Foreign Application Priority Data
Mar. 12, 2020 (FR) ...................................... 2002472

(51) Int. Cl.
*G06F 3/01* (2006.01)
*A61B 5/296* (2021.01)
(Continued)

(52) U.S. Cl.
CPC .............. *G06F 3/015* (2013.01); *A61B 5/296* (2021.01); *A61B 5/397* (2021.01); *A61B 5/6824* (2013.01);
(Continued)

(58) Field of Classification Search
None
See application file for complete search history.

(56) References Cited

U.S. PATENT DOCUMENTS

2014/0198034 A1    7/2014  Bailey et al.
2018/0070864 A1*   3/2018  Schuster ................ G16H 40/63
(Continued)

OTHER PUBLICATIONS

International Search Report dated Jun. 11, 2021 in corresponding International Patent Application No. PCT/EP2021/056373; 6 pages (including English translation).
(Continued)

*Primary Examiner* — Stephen T. Reed
(74) *Attorney, Agent, or Firm* — Maier & Maier, PLLC (57) ABSTRACT

A method for controlling a limb of a virtual avatar by the myoelectric activities of a limb of an individual. The method includes a first step of calibrating and second step of moving the limb of the virtual avatar. Also, a system suitable for implementing the method for controlling a limb of a virtual avatar by the myoelectric activities of a limb of an individual.

11 Claims, 3 Drawing Sheets

(51) Int. Cl.
*A61B 5/397* (2021.01)
*A61B 5/00* (2006.01)
*A61F 2/72* (2006.01)

(52) U.S. Cl.
CPC ............ *A61B 5/744* (2013.01); *G06F 3/016* (2013.01); *A61B 2560/0223* (2013.01); *A61F 2/72* (2013.01)

(56) References Cited

U.S. PATENT DOCUMENTS

2019/0247650 A1* 8/2019 Tran ................ A61N 1/3704
2021/0349529 A1* 11/2021 Winold ............. A61B 5/1124
2023/0023609 A1* 1/2023 Winold ............. A63B 71/0622

OTHER PUBLICATIONS

Tabor et al., "Designing Game Based Myoelectric Prosthesis Training", Proceedings of the 2017 CHI Conference on Human Factors in Computing Systems, CHI'17, ACM Press, New York, USA, May 2, 2017, pp. 1352-1363.

Patel et al., "Context-Dependent Adaptation Improves Robustness of Myoelectric Control for Upper-Limb Prostheses", J. of Neural Engineering, Institute of Physics Publishing, Bristol, GB, vol. 14, No. 5, Sep. 20, 2017, pp. 1-22.

* cited by examiner

METHOD FOR CONTROLLING A LIMB OF A VIRTUAL AVATAR BY MEANS OF THE MYOELECTRIC ACTIVITIES OF A LIMB OF AN INDIVIDUAL AND SYSTEM THEREOF

FIELD

The present invention relates to a method for controlling a limb of a virtual avatar by the myoelectric activities of a limb of a subject.

The present invention relates in particular to the population of persons who are victims of amputations and in particular amputations of the upper limb.

BACKGROUND

Some amputated persons have a myoelectric prosthesis, i.e. a contact prosthesis the movements of which are controlled by means of electrical signals coming from the muscles of the user.

One of the main problems encountered by patients wearing myoelectric prostheses is the cognitive load associated with the control and the permanent visual slaving that is required by use thereof.

The myoelectric control necessary for controlling prostheses is based on the activation of two antagonistic muscles and on the quality of the dissociation of the control of these muscles. Such a control is lengthy and requires a great deal of training.

The action is made all the more difficult since the patients have no information on the state of the prosthesis other than that offered by visual feedback. They must remain concentrated on an object to be reached and monitor the action that the prosthesis is in the process of doing. This is extremely expensive in terms of cognitive resources, such as concentration and muscle control. Because of this, many patients abandon their prostheses, which become what is commonly referred to as "cupboard prostheses".

For these various reasons, prostheses are at the present time underused compared with their capabilities.

The article by Tabor et al: "Designing Game-Based Myoelectric Prosthesis Training" in Design and Cognitive Impairment, 2017, relates to a game developed for training amputated persons to use their myoelectric prosthesis. This document discloses the development of a visual interface ("The Falling of Momo"). The character in the game is controlled by means of a bracelet with electrodes placed on the amputated limb, in accordance with a proportional control identical to that of the control of myoelectric prostheses. The intensity of the muscle contraction perceived by the electrodes is proportional to the movement of the character in the game, offering visual feedback to the user.

US 2014/198034 discloses a bracelet with electrodes for use thereof with integrated-screen spectacles operating by recognition of gestures. The muscle contractions perceived by the electrodes during predetermined gestures, for example tensioning the index finger and bending or extending the wrist, make it possible to perform actions on the screen of the spectacles, for example to move a scroll-down menu. Recognition of gestures can be confirmed by haptic feedback, by applying a discrete two-state signal at the end of the gesture).

The article by Patel et al: "Context-dependent adaptation improves robustness of myoelectric control for upper-limb prostheses" in Journal of Neural Engineering vol. 14, no. 5 (2017), describes a protocol for improving control of a forearm myoelectric prosthesis by means of a bracelet with electrodes and in accordance with a learning model. The signals obtained by the electrodes are processed in order to obtain the envelope thereof. The envelopes of the muscle-activity signals are used in a gesture-recognition algorithm. The output signal of this algorithm is an estimation of the standardised activation level associated with a function of the prosthesis, for example opening the hand or rotating the wrist. On the basis of this output signal, an activity threshold and a gain are calculated in order to define the control information sent to the prosthesis in order to move it. The activity threshold is modified in order to avoid parasitic activities of the other functions. The gain is fixed by a function.

SUMMARY

One aim of the present invention is to propose a method for improving learning of the muscle dissociation and the fine work of muscle contractions.

For this purpose, the object of the present invention is a method for controlling a limb of a virtual avatar by the myoelectric activities of a limb of a subject, comprising a first calibration step comprising:
  acquiring first and second raw calibration myoelectric activity signals by a device for measuring myoelectric activity signals, the first and second raw calibration myoelectric activity signals resulting from contractions of variable intensities of first and second antagonistic muscles of the limb of the subject respectively, during a given period, and then, for each of the two antagonistic muscles:
  determining the envelope of the signal,
  determining the minimum and maximum myoelectric activities from the envelope of the signal,
  determining a myoelectric activity threshold,
  normalizing the maximum myoelectric activity and the myoelectric activity threshold,
  determining a coefficient of conversion of the normalized myoelectric activity into a component of speed of movement of a limb of the virtual avatar, and the method for controlling comprising a second step of moving the limb of the virtual avatar comprising:
  acquiring first and second raw myoelectric activity signal by the device for measuring myoelectric activity signals, the first and second raw myoelectric activity signals resulting from contractions of the two antagonistic muscles of the limb of the subject, during a given period, and then, for each of the first and second raw myoelectric activity signals:
  normalizing the myoelectric activity resulting from the signal,
  converting the normalized myoelectric activity into a component of speed of movement of a limb of a virtual avatar by applying the coefficient of conversion,
  determining a speed and a direction of movement of the limb of the virtual avatar by subtracting the movement speed components obtained for each of the muscles, and
  moving the limb of the virtual avatar with the determined speed and direction of movement.

According to other advantageous aspects of the invention, the method comprises one or more of the following features, taken in isolation or in accordance with any technically possible combination:
  simultaneously with the step of moving the limb of the virtual avatar with the determined speed and direction of movement, the method comprises the activation of a sensory feedback device disposed on the limb of the subject, the sensory feedback device being activated selectively and discretely according to predetermined ranges of values of a sensory parameter;

the sensory parameter is selected from a bending angle of an elbow of the virtual avatar, an anterior elevation angle of a shoulder of the virtual avatar, an abduction/adduction angle of the shoulder of the virtual avatar, a medial or lateral rotation angle of the shoulder of the virtual avatar, a bending angle of a wrist of the virtual avatar, a radial or ulnar rotation angle of the virtual avatar, a degree of opening of a hand of the virtual avatar, a degree of opening of a finger grip involving the thumb and one or more other fingers of the hand of the virtual avatar, a gripping force of a hand of the virtual avatar, a bending angle of a knee of the virtual avatar, a bending angle of the ankle of the virtual avatar, a speed of rotation of one of the movements mentioned in the present list, or any other sensory modality able to be replaced by vibrations, such as the warmth or configuration of the prosthesis, the device for measuring myoelectric activity signals comprises a plurality of electrodes, the method comprising selecting two electrodes from the plurality of electrodes enabling a maximum acquisition of the myoelectric activity signals of each of the two antagonistic muscles;

the steps of determining the minimum and maximum myoelectric activities from the raw calibration myoelectric activity signal acquired, of determining a myoelectric activity threshold, of normalizing the maximum myoelectric activity and the myoelectric activity threshold, of determining a coefficient of conversion of the normalized myoelectric activity into a component of speed of movement of a limb of the virtual avatar, of normalizing the myoelectric activity resulting from each of the first and second signals, of converting the standardised myoelectric activity into a component of speed of movement of a limb of a virtual avatar by applying the coefficient of conversion, of determining a speed and a direction of movement of the limb of the virtual avatar by subtracting the movement speed components obtained for each of the muscles, and of moving the limb of the virtual avatar with the determined speed and direction of movement are implemented by a processing device;

determining the minimum myoelectric activities from the envelope of the signal comprises:

setting the raw calibration myoelectric activity signal to a zero mean value, determining the absolute value of the raw calibration myoelectric activity signal set to zero mean value, filtering the signal in absolute value to obtain the envelope thereof, and from the envelope of the filtered signal, determining the minimum value and the maximum value of the envelope of the filtered signal.

According to another aspect, the object of the present invention is a method for controlling a limb of a virtual avatar by the myoelectric activities of a limb of a subject, comprising a first calibration step comprising:

acquiring first and second raw calibration myoelectric activity signals by a device for measuring myoelectric activity signals, the first and second raw calibration myoelectric activity signals resulting from contractions of variable intensities of first and second antagonistic muscles of the limb of the subject respectively, during a given period, then:

determining the envelope of each of the first and second signals by a processing device, determining the minimum and maximum myoelectric activities from the envelope of each of the first and second signals by the device processing the signal, and then, for each of the two antagonistic muscles, determining a myoelectric activity threshold by the processing device, normalizing the maximum myoelectric activity and the myoelectric activity threshold by the processing device, determining a coefficient of conversion of the normalized myoelectric activity into a component of speed of movement of a limb of the virtual avatar by the processing device, and the method for controlling comprising a second step of moving the limb of the virtual avatar comprising:

acquiring first and second raw myoelectric activity signal by the device for measuring myoelectric activity signals, the first and second raw myoelectric activity signals resulting from contractions of the two antagonistic muscles of the limb of the subject, during a given period, and then, for each of the first and second raw myoelectric activity signals, normalizing the myoelectric activity resulting from the signal by the processing device, converting the normalized myoelectric activity into a component of the speed of movement of a limb of a virtual avatar by applying the coefficient of conversion by the processing device, determining a speed and direction of movement of the limb of the virtual avatar by subtracting movement speed components obtained for each of the muscles by the processing device, and moving the limb of the virtual avatar with the speed and direction of movement determined by the processing device.

Another object of the invention is a system adapted for implementing the method for controlling a limb of a virtual avatar by the myoelectric activities of a limb of a subject according to the invention, the system comprising:

a device for measuring myoelectric activity signals resulting from contractions of first and second antagonistic muscles of the limb of the subject, suitable for acquiring first and second raw calibration myoelectric activity signals resulting from contractions of variable intensities of a first and a second antagonistic muscle of the limb of the subject respectively, during a given period, and first and second raw myoelectric activity signal resulting from contractions of the two antagonistic muscles of the limb of the subject, during a given period, a processing device for processing the myoelectric activities comprising at least one display device configured for displaying the virtual avatar, the processing device being configured for determining the minimum and maximum myoelectric activities from an acquired raw calibration myoelectric activity signal, determining a myoelectric activity threshold, normalizing the maximum myoelectric activity and the myoelectric activity threshold, determining a coefficient of conversion of the normalized myoelectric activity into a component of speed of movement of a limb of the virtual avatar, normalizing the myoelectric activity resulting from each of the first and second signals, converting the normalized myoelectric activity into a component of speed of movement of a limb of a virtual avatar by applying the coefficient of conversion, determining a speed and a direction of movement of the limb of the virtual avatar by subtracting the movement speed components obtained for each of the muscles, and moving the limb of the virtual avatar with the determined speed and in the direction of movement.

According to other advantageous aspects of the invention, the system comprises one or more of the following features, taken in isolation or in accordance with any technically possible combination:

- the device for measuring comprises a plurality of electrodes and is in the form of a bracelet;
- the system furthermore comprises a sensory feedback device;
- the sensory feedback device comprises a plurality of vibrating elements;
- the processing device is configured for activating the sensory feedback device selectively and discretely according to predetermined ranges of values of a sensory parameter;
- the device for measuring myoelectric activity signals comprises a remote communication device configured for remotely communicating with the processing device.

Another object of the invention is a system adapted for implementing the method for controlling a limb of a virtual avatar by the myoelectric activities of a limb of a subject according to the invention, the system comprising:

- a device for measuring myoelectric activity signals resulting from contractions of first and second antagonistic muscles of the limb of the subject, suitable for acquiring first and second raw calibration myoelectric activity signals resulting from contractions of variable intensities of first and second antagonistic muscles of the limb of the subject respectively, during a given period, and first and second raw myoelectric activity signal resulting from contractions of the two antagonistic muscles of the limb of the subject, during a given period,
- a processing device for processing the myoelectric activities comprising at least one display device configured for displaying the virtual avatar,
- the processing device being configured for, in a first calibration step, determining the envelope of each of the first and second signals, determining the minimum and maximum myoelectric activities from the envelope of each of the first and second signals, determining a myoelectric activity threshold, normalizing the maximum myoelectric activity and the myoelectric activity threshold, determining a coefficient of conversion of the normalized myoelectric activity into a component of speed of movement of a limb of the virtual avatar, normalizing the myoelectric activity resulting from each of the first and second signals, converting the normalized myoelectric activity into a component of speed of movement of a limb of a virtual avatar by applying the coefficient of conversion, and, in a second step of moving the limb of the virtual avatar, for each of the first and second raw myoelectric activity signals: normalizing the myoelectric activity resulting from the signal, converting the normalized myoelectric activity into a component of speed of movement of a limb of a virtual avatar by applying the coefficient of conversion, determining a speed and a direction of movement of the limb of the virtual avatar by subtracting the movement speed components obtained for each of the muscles, and moving the limb of the virtual avatar with the determined speed and direction of movement.

BRIEF DESCRIPTION OF THE DRAWINGS

These features and advantages of the invention will emerge from the reading of the following description, given solely by way of non-limitative example, and made with reference to the accompanying drawings, on which.

DETAILED DESCRIPTION

Figure 1:
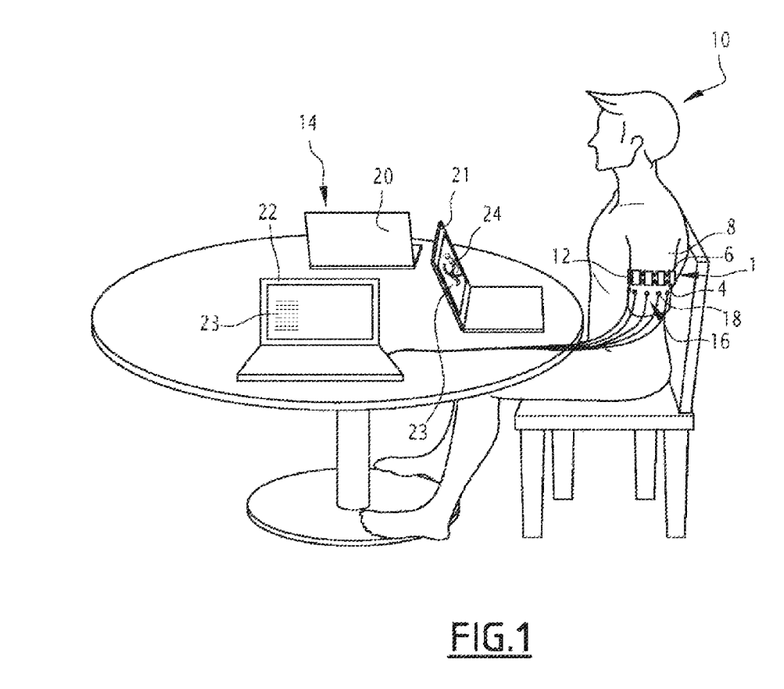
FIG. 1 is a schematic view of a system according to one embodiment of the invention.

On FIG. 1, a system 1 adapted for implementing the method according to the invention is shown.

The system 1 comprises a device 4 for measuring myoelectric activity signals. The myoelectric activity signals come from electric influxes transmitted by nerve fibres to a muscle and causing the contraction of this muscle.

The device 4 for measuring comprises a plurality of electrodes 6. The electrodes 6 are for example three-phase surface electrodes adapted for being placed on a limb 8 of a subject 10 and receiving the myoelectric activity signals coming from the muscles of the limb 8 of this subject 10.

The electrodes 6 are typically configured for acquiring myoelectric activity signals.

In particular, the electrodes 6 are configured for acquiring first and second raw calibration myoelectric activity signals resulting from contractions of variable intensities of first and second antagonistic muscles, for example the biceps and the triceps.

The electrodes 6 are typically furthermore configured for acquiring first and second raw myoelectric activity signals resulting from contractions of the first and second antagonistic muscles of the limb 8 of the subject 10, during a given period.

In particular, the device 4 for measuring myoelectric activity signals includes eight electrodes 6.

The acquisition frequency of the electrodes 6 is for example 200 Hz. Such a frequency is particularly adapted for obtaining the envelope of the signal.

However, other frequency values can be envisaged, for example comprised between 100 Hz and 2000 Hz in order to obtain more precise signals.

The device 4 for measuring is typically in the form of a flexible bracelet. Such a form makes it possible to place the measuring device 4 around a limb 8, the limb 8 being for example an arm, the remaining part of a forearm or stump, or of an arm. The electrodes 6 are then disposed in a circle and towards the interior of the circle.

The electrodes 6 are connected together by any material adapted for forming a bracelet. The bracelet is for example extensible. According to a variant, the bracelet comes in several sizes adapted to different morphologies and for adapting both to the upper limb and to the lower limb. The bracelet may furthermore comprise a closure device, for example a self-gripping system, a buckle, press studs or any other option that can be envisaged.

Figure 2:
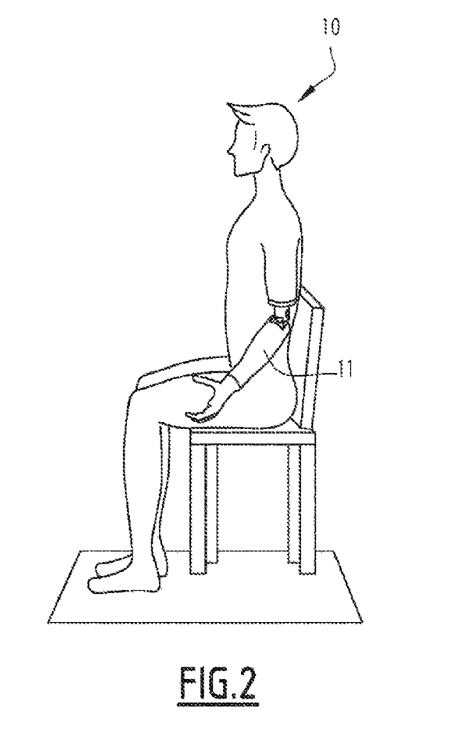
FIG. 2 is a schematic view of a subject wearing a myoelectric prosthesis.

Other forms of the device 4 for measuring can be envisaged, for example the electrodes are not connected together, or the device 4 for measuring is integrated in a myoelectric prosthesis 11 as can be seen in FIG. 2. Myoelectric prosthesis means a contact prosthesis operating by means of myoelectric activity signals and controlled by its user.

The system 1 also comprises a remote communication device 12.

The remote communication device 12 is typically a radio communication device.

For example, the remote communication device 12 is a Bluetooth or Wi-Fi communication device.

The remote communication device 12 is configured for transmitting the myoelectric activities read by the electrode 6 to a device 14 for processing the myoelectric activities.

According to an advantageous embodiment, the system 1 also comprises a sensory feedback device 16.

The sensory feedback device 16 comprises for example a plurality of vibrating elements 18.

The sensory feedback device 16 is typically in the form of a bracelet. For example, the sensory feedback device 16 is in the form of an elastic bracelet. The sensory feedback device 16 and the device 4 for measuring are preferably secured together.

For example, the sensory feedback device 16 comprises sixteen vibrating elements 18. In a variant, the sensory feedback device 16 comprises a different number of vibrating elements 18, for example six vibrating elements.

The sensory feedback device 16 makes it possible to offer a sensory feedback to the subject 10 following a muscle contraction causing the detection of a myoelectric activity by the electrodes 6. The operation thereof will be explained later.

The processing device 14 comprises at least one processor. The processing device 14 furthermore comprises a memory suitable for recording the myoelectric activities read.

The processing device 14 shown on FIG. 1 comprises three computers 20, 21, 22.

The processing device 14 preferably comprises at least one display device 23.

On FIG. 1, each computer 20, 21, 22 comprises a display device 23. The display device 23 is typically a screen.

The three computers 20, 21, 22 are configured for communicating with each other, for example by means of a switch configured to interact in a local area network.

The device 4 for measuring myoelectric activity signals is configured for communicating remotely with the processing device 14. In the example in FIG. 1, the device 4 for measuring is configured for communicating remotely with a first computer 20.

The first master computer 20 is configured for receiving the raw myoelectric activity signals acquired by the electrodes 6 and transmitted by the remote communication device 12, processing said raw myoelectric activity signals and transmitting the processed myoelectric activity signals, in particular to a second computer 21 and to a third computer 22.

Advantageously, the first computer 20 is configured for identifying two electrodes 6 of the measuring device 4 allowing maximum acquisition of the myoelectric activity signals from each of the two antagonistic muscles.

The first computer 20 is configured for determining minimum and maximum myoelectric activities for each of the two antagonistic muscles from an acquired raw calibration myoelectric activity signal.

For this purpose, the first computer 20 is also adapted for setting the raw calibration myoelectric activity signal acquired by the electrodes 6 to a zero mean value.

The first computer 20 is furthermore configured for determining the absolute value of the raw calibration myoelectric activity signal set to zero mean value.

The first computer 20 is configured for filtering the signal in absolute value to obtain the envelope thereof.

For example, the first computer 20 comprises a Butterworth filter of the second order low-pass type with a cut-off frequency of 1.5 Hz configured for filtering the signal obtained to obtain the envelope thereof.

The first computer 20 is adapted for determining a myoelectric activity threshold, referred to as EMGx offset, below which the contraction of the muscle is not obligatorily intentional and must not be taken into consideration in order to avoid disturbing a movement produced.

The first computer 20 is configured to take into account only the values recorded between the given threshold and the maximum value of the envelope of the filtered signal.

The first computer 20 is configured for normalizing the values of the envelope of the filtered signal.

The first computer 20 is typically configured for attributing the value zero to the myoelectric activity threshold previously calculated, and for attributing the value 1 to the maximum value of the envelope of the filtered signal.

In particular, the first computer 20 is configured for determining a coefficient for converting the normalized myoelectric activity into a component of speed of movement of a limb of a virtual avatar 24.

For example, the conversion coefficient is determined in the following manner for the movement of the arm of the avatar. Conventionally, the very quick rotation of the elbow is of 4 rad/s. This value is taken as a starting point, and the subject 10 gives his perception with regard to this speed. The coefficient of conversion is increased or decreased so that the perception of speed is in agreement with the muscle activity of the subject 10. This coefficient is particular to each muscle.

The first computer 20 is typically configured for attributing, for each muscle, a zero speed component when the normalized value attributed to the value of the envelope of the filtered signal is 0, and for attributing a maximum speed component when the value attributed to the normalized value of the envelope of the filtered signal is 1.

In particular, the first computer 20 is able to attribute, for each muscle, to each normalized value of the envelope of the filtered signal, a speed component lying between the zero speed component and the maximum speed component.

The first computer 20 is furthermore configured for converting the normalized myoelectric activity into a component of speed of movement of the limb of the virtual avatar 24 by applying the coefficient of conversion.

The first computer 20 is configured for determining a speed and direction of movement of the limb of the virtual avatar 24 displayed by the second computer 21 by subtracting the speed components obtained for each of the muscles at a given instant. For example, in the case of the rotation of an elbow, subtracting the speed values makes it possible to determine a bending or extension speed of an elbow of a virtual avatar 24 displayed by the display device 23 of the second computer 21.

The display device 23 of the second computer 21 is configured for displaying the virtual avatar 24 showing at least one limb corresponding to the movement that must be controlled by the myoelectric activities. It may be a case of the arm or a limb, a complete body or a half body according to the application chosen.

Stopping the muscle contractions causes for example stopping of the movement, positioning of the elbow of the virtual avatar 24 is then in a fixed position that corresponds to the last position reached.

According to alternatives, the calculated speed is a speed of opening or closing of a hand of a virtual avatar, or a speed of rotation of the wrist of a virtual avatar, or a speed of bending/extension of a knee or ankle of a virtual avatar, or any other option that can be envisaged.

The first computer 20 is configured for transmitting a movement command to the second computer 21.

The movement command typically comprises the determined movement speed and direction.

Preferably, the first computer 20 is configured for determining a sensory parameter of the limb of the virtual avatar 24 to be associated with at least one vibrating element 18 and to retransmit in vibrations.

The sensory parameter is for example selected from a bending angle of an elbow of the virtual avatar 24, an anterior elevation angle of a shoulder of the virtual avatar 24, an abduction/adduction angle of the shoulder of the virtual avatar 24, a medial or lateral rotation angle of the shoulder of the virtual avatar 24, a bending angle of a wrist of the virtual avatar 24, a radial or ulnar rotation angle of the virtual avatar 24, a degree of opening of a hand of the virtual avatar 24, a degree of opening of a finger grip involving the thumb and one or more other fingers of the hand of the virtual avatar 24, a gripping force of a hand of the virtual avatar 24, a bending angle of a knee of the virtual avatar 24, a bending angle of the ankle of the virtual avatar 24, a speed of rotation of one of the movements mentioned in the present list, or any other sensory modality able to be substituted by vibrations, such as the warmth or configuration of a myoelectric prosthesis 11 of the subject 10.

Configuring the myoelectric prosthesis 11 corresponds to the selection of one of the modes of the myoelectric prosthesis 11 during use to know on which joint the muscle activation will act. For example, if the prosthesis is in a mode called "pronosupination of the wrist", the vibrations will signal the pronosupination movement of the wrist. Likewise, in a mode called "elbow", the vibrations will signal the movements of the elbow.

The second computer 21 is dedicated to the visual interface with the subject 10.

According to an alternative that is not shown, the second computer is directly integrated in the first computer 20. This makes it possible to reduce the number of interfaces.

The second computer 21 is configured for receiving the movement command transmitted by the first computer 20.

In an advantageous embodiment, the third computer 22 is configured for activating the sensory feedback device 16.

According to an alternative that is not shown, the third computer is directly integrated in the electrode bracelet 6 by means of a microcontroller and with a control system by pulse width modulation.

The first computer 20 is configured for sending to the third computer 22 the processed myoelectric activities converted into an instantaneous value of the sensory parameter by applying the coefficient of conversion.

The third computer 22 is typically configured for determining ranges of values of the sensory parameter to be associated with at least one vibrating element 18.

The third computer 22 is typically configured for activating at least one element 18 corresponding to a range of values of the sensory parameter previously determined.

The third computer 22 comprises for example a reading program configured for making a match between the instantaneous value of the sensory parameter and the activation of the corresponding vibrating element 18.

The third computer 22 is then configured for activating the corresponding vibrating element 18.

The sensory feedback device 16 is connected to the third computer 22, for example by means of cables.

In the alternative where the third computer 22 is directly integrated in the bracelet of electrodes 6, the electrodes 6, the sensory feedback device 16 and the third computer 22 are grouped together.

Preferably, the third computer 22 is configured for activating the vibrating elements 18 selectively and discretely.

For example, the third computer 22 is able to determine the number and position of the vibrating elements 18 to be activated according to ranges of values of a selected sensory parameter.

Preferably, in each range of values of the sensory parameter, a single determined vibrating element 18 is activated.

Preferably again, a single vibrating element 18 distinct for each range of values is attributed to a range of values of the sensory parameter.

According to the example where the sensory parameter is the bending angle of the elbow, when the subject 10 contracts the biceps and/or triceps, the electrodes 6 are configured for acquiring first and second raw myoelectric activity signals resulting from contractions of the biceps or of the triceps, respectively; during a given period, the remote communication device 12 is configured for transmitting the first and second raw myoelectric activity signals to the first computer 20, the first computer 20 is configured for processing the first and second raw myoelectric activity signals and for transmitting to the second computer 21 a command for moving the arm of the virtual avatar 24 and to the third computer 22 an instantaneous position of the arm of the virtual avatar 24, the second computer 21 is configured for displaying the movement of the arm of the virtual avatar 24 and the third computer 22 is configured for activating each vibrating element 18 in steps of 20° of elbow bending angle. Naturally the step may have a value different from 20°, for example 10°, 15°, 25°, 30°.

The third computer 22 is preferably configured for determining the duration and the sequence of the vibrations.

For example, the third computer 22 is configured for activating a given vibrating element 18 during a period of 100 ms alternating with a stop for a period of 100 ms.

The vibration intensity is preferably adaptable to improve the comfort of the subject 10.

In an alternative, the processing device 14 comprises a single computer, or a smartphone, a television or a tablet, or any combination of these elements that can be envisaged. For example, all the functions of the first, second and third computers described above are able to be implemented by this single computer.

According to another alternative, the processing device is at least partially incorporated in a device for measuring. For example, the incorporated part of the processing device is configured for implementing all the functions of the first and second computers described above.

A method for controlling a limb of a virtual avatar by the myoelectric activities of a limb of a subject will now be described. The method is implemented by the system 1.

The device 4 for measuring myoelectric activity signals is placed on a limb 8 of the subject 10 so that the electrodes 6 are in contact with first and second antagonistic muscles of this limb.

For example, the subject 10 is a person with a limb amputated. The subject 10 has for example had an arm amputated and has a transhumeral amputation, i.e. above the elbow. The device 4 for measuring myoelectric activity signals is placed around the amputated arm of the subject 10 so that the electrodes 6 are in contact with the biceps and triceps, two antagonistic muscles.

In an alternative, the subject does not have an amputation and the device for measuring myoelectric activity signals is placed around the arm of the subject so that the electrodes are in contact with the biceps and triceps. The non-amputated subject has the arm immobilised in a device. This makes it possible to reproduce the muscle situation of an amputated subject, i.e. an isometric contraction of the biceps and of the triceps characterised by an absence of movement.

The method comprises a first calibration step.

The electrodes 6 acquire first and second raw calibration myoelectricity signals, the first and second raw calibration myoelectric activity signal resulting from contractions of variable intensities of the first and second antagonistic muscles of the limb 8 of the subject 10, respectively, during a given period.

The device 4 for measuring myoelectric activity signals communicates remotely with the processing device 14 by means of the remote communication device 12. In the example in FIG. 1, the device 4 for measuring communicates remotely with the first computer 20.

Advantageously, the method furthermore comprises the identification of two electrodes 6 of the measuring device 4 allowing a maximum acquisition of the myoelectric activity signals of each of the two antagonistic muscles. To do this, the subject 10 makes dissociated contractions of the two antagonistic muscles wearing the measuring device 4, for example, the biceps and the triceps.

Each electrode 6 acquires a raw calibration myoelectric activity signal that it transmits to the processing device 14 by means of the remote communication device 12.

The acquisition frequency of the electrode 6 is for example 200 Hz.

Once the contractions have been made, the acquisition is stopped and the processing device 14 selects the two electrodes 6 that each acquired its own significant activity during the activation of one of the antagonistic muscles and that did not acquire, or only slightly acquired, co-contraction activities.

Co-contraction activities correspond to a simultaneous contraction of the two antagonistic muscles.

In particular, the first computer 20 selects the two electrodes 6 allowing a maximum acquisition of the raw calibration myoelectric activity signals of each of the two antagonistic muscles.

After identification of two electrodes 6 allowing maximum acquisition, the method comprises the determination, in particular by the processing device 14, of the minimum and maximum myoelectric activities for each of the two antagonistic muscles from the acquired raw calibration myoelectric activity signal.

In particular, the first computer 20 determines minimum and maximum myoelectric activities for each of the two antagonistic muscles from the acquired raw calibration myoelectric activity signal.

To do this, the subject 10 makes for example the strongest muscle contraction possible of the first muscle, for example of the biceps, for a given period, and then relaxes. The given period is between one second and three seconds, preferably equal to two seconds. Then the subject 10 makes the strongest muscle contraction possible of the second muscle, for example of the triceps, for a given period, and then relaxes. The given period is for example two seconds.

First and second raw calibration myoelectric activity signals resulting from these contractions are acquired by the electrodes 6.

The remote communication device 12 transmits the raw calibration myoelectric activity signal to the processing device 14.

In particular, the remote communication device 12 transmits the raw calibration myoelectric activity signal to the first computer 20.

The processing device 14 then sets the raw calibration myoelectric activity signal to zero mean value.

In particular, the first computer 20 sets the raw calibration myoelectric activity signal to zero mean value.

The processing device 14 determines the absolute value of the raw calibration myoelectric activity signal set to zero mean value.

In particular, the first computer 20 determines the absolute value of the raw calibration myoelectric activity signal set to zero mean value.

The processing device 14 filters the signal in absolute value to obtain the envelope thereof.

In particular, the first computer 20 filters the signal in absolute value to obtain the envelope thereof.

For example, the filter used is a Butterworth filter of the second order low-pass type with a cut-off frequency of 1.5 Hz.

From the envelope of the filtered signal, the processing device 14 determines, for each of the two antagonistic muscles, the minimum value and the maximum value of the envelope of the filtered signal.

In particular, the first computer 20 determines, for each of the two antagonistic muscles, the minimum value and the maximum value of the envelope of the filtered signal.

The minimum value and the maximum value of the envelope of the filtered signal correspond to the minimum and maximum myoelectric activities.

Advantageously, the processing device 14 stores the minimum value and the maximum value of the envelope of the filtered signal.

Then the processing device 14 determines a myoelectric activity threshold, called EMGx offset, below which the contraction of the muscle is not obligatorily intentional and must not be taken into consideration in order to avoid disturbing the acquired movement. This is because values located below this threshold correspond to a residual activity of the muscles following muscle fatigue, and could disturb the movement.

In particular, in determining this threshold account is taken of the perception of the subject 10 and is calculated as follows, for each of the two antagonistic muscles:

$$\text{offset } EMG_x = \text{perc}_x * (EMG_{x\ max} - EMG_{x\ min}) + EMG_{x\ min}, \text{with}$$

offset $EMG_x$ the threshold of myoelectric activity;
$\text{perc}_x$ the percentage over the extent of the muscle activity;
$EMG_{x\ max}$ the maximum value of the envelope of the filtered signal, and
$EMG_{x\ min}$ the minimum value of the envelope of the filtered signal.

The percentage over the extent of the muscle activity of the subject 10 is determined so that the speed of movement of the limb of the virtual avatar is zero when the subject feels relaxed.

Typically, this percentage is between 4% and 10%.

This percentage has an impact when the subject wishes to generate a speed of movement of the limb of the virtual avatar but also to cancel out this speed.

This percentage is refined for each muscle.

The myoelectric activity threshold value is typically determined by default at 5% of the extent of the muscle activity.

Next, this myoelectric activity threshold is typically tested and adjusted with the subject 10 in order to assess whether it is disturbing the control of the virtual avatar 24.

Preferably, the value of the myoelectric activity threshold can be adjusted at any moment and in particular after several minutes of work, where muscle fatigue may make itself felt and the residual muscle activity become a problem.

In particular, the first computer 20 determines the myoelectric activity threshold.

From the determination of the myoelectric activity threshold, the first computer 20 will take into account only the values recorded between the given threshold and the maximum value of the envelope of the filtered signal.

Advantageously, the processing device 14 stores the myoelectric activity threshold.

Then the processing device 14 normalizes the determined threshold and the maximum value of the envelope of the filtered signal.

In particular, the first computer 20 normalizes the determined threshold and the maximum value of the envelope of the filtered signal.

The first computer 20 typically attributes the value 0 to the myoelectric activity threshold previously calculated, and the value 1 to the maximum value of the envelope of the filtered signal.

The processing device 14 determines, for each muscle, a coefficient of conversion making it possible to convert any normalized value of the envelope of the filtered signal lying between the determined threshold and the maximum value of the envelope of the filtered signal into a speed component. The coefficient of conversion is adapted to the subject for each of the muscles in order to make the perception of movement as faithful as possible. The coefficient of conversion typically makes it possible to attribute, for each muscle, a zero speed component when the normalized value of the envelope of the filtered signal is 0, and to attribute a maximum speed component when the normalized value of the envelope of the filtered signal is 1.

Advantageously, the processing device 14 stores the coefficient of conversion.

Such a calibration of the recorded myoelectric activity signals allows a fine adjustment of the control of the virtual avatar 24 adapted to the subject 10 in particular when the myoelectric activities are very unequal between the two antagonistic muscles.

After this calibration phase, the method comprises a step of moving the limb of the virtual avatar 24.

The system 1 is ready to acquire new myoelectric activity signals and to process them.

The two selected electrodes 6 acquire first and second raw myoelectric activity signals resulting from contractions of the two antagonistic muscles of the limb 8 of the subject 10, for a given period.

For each of the first and second raw myoelectric activity signals, the remote communication device 12 transmits the raw myoelectric activity signal to the first computer 20.

The first computer 20 sets the raw myoelectric activity signal to zero mean value.

The first computer 20 determines the absolute value of the raw myoelectric activity signal set to zero mean value.

The first computer 20 filters the signal in absolute value to obtain the envelope thereof.

The first computer 20 normalizes the values of the envelope of the filtered signal, for example by a rule of three, from the myoelectric activity threshold previously calculated and stored, and from the maximum value of the envelope of the filtered signal previously determined and stored to obtain a value of between 0 and 1.

The first computer 20 typically attributes, for each muscle, to each normalized value of the envelope of the filtered signal, a speed component lying between the zero speed component and the maximum speed component, by applying the coefficient previously determined and stored.

The first computer 20 determines a speed and a direction of movement of a limb of the virtual avatar 24 displayed by the second computer 21 by subtracting the speed components obtained for each of the muscles.

For example, in the case of the rotation of an elbow, subtracting the speed values makes it possible to determine a bending or extension speed of an elbow of a virtual avatar 24 displayed by the second computer 21.

The first computer 20 transmits a movement command to the second computer 21.

The movement command typically comprises the determined speed and direction of movement of the limb of the virtual avatar 24.

The second computer 21 receives the movement command transmitted by the first computer 20.

The display device 23 of the second computer 21 displays the virtual avatar 24 showing at least one limb corresponding to the movement that must be controlled by the myoelectric activities. It may be a case of the arm or a leg, an entire body or a half body according to the selected application.

The limb of the virtual avatar 24 moves according to the movement command transmitted by the first computer 20.

For example, stopping the muscle contractions causes stopping of the movement, positioning of the elbow of the virtual avatar 24 is then in a fixed position that corresponds to the last position reached.

Thus, when the subject 10 contracts at least one of the muscles on which the electrodes 6 are placed, the virtual avatar 24 bends or extends his elbow according to the adjustments made adapted to the subject.

According to alternatives, the calculated speed is a speed of opening or closing of a hand of a virtual avatar, or a speed of rotation of a wrist of a virtual avatar, or a speed of a bending/extension of a knee or of the ankle of a virtual avatar, or any other option that can be envisaged.

The subject 10 thus has a visual feedback of the contractions that he makes with the two antagonistic muscles, by the virtual avatar 24 the movements of which are adapted to the muscle contraction capabilities of the subject. Learning of muscle dissociation and the fine work of the muscle contractions are thus improved.

In an advantageous embodiment of the method, after having determined a speed of movement and a direction of movement of the limb of the virtual avatar 24 by acquiring the first and second myoelectric activity signals, the method comprises the activation of the sensory feedback device 16, in particular by the processing device 14.

The vibrating elements 18 of the sensory feedback device 16 are disposed on the limb 8 of the subject 10 comprising the two antagonistic muscles the myoelectric activity of which is measured.

The vibrating elements 18 are for example sixteen in number and disposed in two bands of eight on either side of the electrodes 6.

The vibrating elements 18 are for example activated in the following manner.

For each myoelectric activity signal acquired by the electrodes 6, the first computer 20 determines an instantaneous value of a sensory parameter, for example an instantaneous position of the limb of the virtual avatar 24 from the previously determined speed and direction of movement.

The first computer 20 sends to the third computer 22 the instantaneous value of the sensory parameter of the limb of the virtual avatar 24.

The third computer 22 determines ranges of values of the sensory parameter of the limb of the virtual avatar 24 to be associated with at least one vibrating element 18.

The third computer 22 typically activates at least one element 18 corresponding to a previously determined range of values of the sensory parameter.

In particular, the reading program of the third computer 22 makes the match between the instantaneous value of the first sensory parameter and the activation of the corresponding vibrating element 18.

Preferably the third computer 22 activates the vibrating elements 18 selectively and discretely.

For example, the third computer 22 determines the number and position of the vibrating elements 18 to be activated according to the range of values of the sensory parameter.

Preferably, in each range of values of the sensory parameter.

Preferably again, a single vibrating element 18 distinct for each range of values of the sensory parameter is attributed to a range of values of the sensory parameter.

According to the example where the sensory parameter is the bending angle of the elbow, when the subject 10 contracts the biceps and/or the triceps, the electrodes 6 acquire first and second raw myoelectric activity signals resulting from contractions of the biceps and of the triceps, respectively, the remote communication device 12 transmits the first and second myoelectric activity signals to the first computer 20, the first computer 20 processes the first and second myoelectric activity signals and transmits to the second computer 21 a command to move the arm of the virtual avatar 24 and to the third computer 22 an instantaneous position of the arm of the virtual avatar 24, the second computer 21 displays the movement of the arm of the virtual avatar 24 and the third computer 22 activates each vibrating element 18 in steps of 20° of bending angle of the elbow. Obviously the step could have a value different from 20°, for example 10°, 15°, 25°, 30°.

This allows the most natural control possible, i.e. both quick in the execution of the movement but also precise to allow stopping on a target without oscillation.

The third computer 22 preferably determines the duration and the sequence of the vibrations for each instantaneous position.

For example, for a given instantaneous position, the third computer 22 activates a given vibrating element 18 for a period of 100 ms alternating with a stop for a period of 100 ms.

The vibration intensity is preferably adaptable to improve the comfort of the subject 10.

For example, a first intensity level is defined by the perception by the subject of a first vibration when the vibration intensity is increased from an absence of vibration. A second intensity level is defined by a change from the perception by the subject of a vibration to the absence of perception of vibration when the vibration intensity is reduced from a high vibration.

A vibration intensity level sufficient to stimulate the subject is calculated by means of the mean between the first and second vibration intensity levels.

According to another example, the vibration intensity varies according to the recorded myoelectric activities. In the case of a gripping force of a hand of the virtual avatar 24, the higher the force the greater the vibration intensity applied.

The sensory feedback by vibration makes it possible to add congruent sensory information to the vision while reducing the attention load on the subject, as illustrated in the example below.

An example of implementation of the method according to the invention will now be described.

Example

Equipment and Participants

The participants comprise subjects with an arm amputated transhumerally, i.e. above the elbow, and non-amputated subjects, referred to as healthy.

The tool used for recovering the electrical activities of the biceps and of the triceps is MyoArm Band® from the company Thalmic. This is a bracelet comprising eight surface electrodes, initially designed to operate by means of an algorithm of a pattern of muscle activities at the forearm. It is used here for recovering the electrical muscle activities of the biceps and of the triceps on the arm of the participants.

A bracelet of six vibrators of 7 mm in diameter and 2 mm thick is used for sending a vibrotactile sensory feedback to the participant.

Three computers are connected together with, for each, a very precise role. The main computer, the master computer, is the carrier of the programs of the whole of the protocol for running the various exercises, and also has the role of (1) receiving the myoelectric activities sent from the MyoArm Band by Bluetooth, (2) processing them, (3) sending to the second computer the movement command translated into a speed (resulting from this processing) so that the elbow of a virtual avatar displayed on the screen of the second computer moves, and (4) sending the instantaneous position calculated from the myoelectric activities to the third computer, which is responsible for activating the vibrators. The exchanges between the master computer and the other two computers are done by means of a switch configured to interact in a local area network.

The second computer is dedicated to the visual interface and placed facing the participant. Animatlab software is used on this computer for displaying the movement of the avatar in real time. In addition, during the exercises, all the instructions are displayed on this computer. The participants merely have to focus on the screen and follow the various instructions.

Finally, the third computer (pi-top) has the role of managing the activation of the vibrators. It receives the instructions from the master computer, indicating to it the position calculated from the myoelectric activities. A reading program on the pi-top makes the match between the position and the activation of the corresponding vibrator. This computer consists of a Raspberry Pi3 to which the bracelet of vibrators is connected.

Calibration

Before any test starts, each participant passes through a necessary calibration phase. During this phase, the muscle activities coming from the eight electrodes of the bracelet are displayed on a graphical interface. It suffices to put on the bracelet and to watch the muscle activities recorded by the electrodes directly. The acquisition frequency of the MyoArm Band is 200 Hz. The raw activity as well as the trace of the filtered signal are visible. During this phase the participants are requested to make dissociated contractions of the biceps and of the triceps.

This makes it possible to identify the two electrodes with which the signal is the clearest for the remainder of the experiment. Once the contractions have been done, the acquisition is stopped and the two electrodes that (i) had an inherent and significant activity during the activation of the biceps or of the triceps and (ii) had no or few co-contraction activities are selected.

Once the electrodes are selected, the minimum and maximum myoelectric activity is determined on each of the channels of the electrodes. For this purpose, the participants are requested to make an almost maximum contraction for 2 seconds of the biceps, and then a relaxation and a contraction of 2 seconds of the triceps.

An avatar with the right arm or the left arm is available according to the laterality of the amputation of the participants. Next, the signal is normalized. A muscle-activity threshold is defined (often between 5% and 7.5% of the extent of the normalized signal) below which no movement would be caused. This makes it possible to prevent the appearance of the residual activity of the muscles following a muscle fatigue that could set the avatar in motion without any real intention by the subject. This threshold can be adjusted during the experiment, giving a certain margin of manoeuvre for adjusting the threshold according to the condition of the participants. Finally, a gain is established between the muscle activity and the speed of rotation of the elbow. This allows a fine adjustment of the control of the avatar, in particular when the muscle activities are very unequal.

Spatial references are defined in order to activate the vibrations by reason of a rapid stimulation made in alternation (activated for 100 ms and then stopped for 100 ms and so on). After a presence (in the precise case of more than 2 seconds) at one of these references, stop time of stimulation is increased in order to stress the participant less while continuing to inform him every 500 ms by an activation of 100 ms.

When the participants contract their muscles, the arm of the virtual avatar moves on the basis of the data coming from the calibration and the vibrators activate in steps of 20° of angle.

Experimentation

Back and forth movements between two targets were requested of the participant in order to evaluate the stability of the control over time. The screen of the second computer displayed the two targets representing the amplitude of the movement in which to move with the arm of the avatar facing the starting target. The amplitudes of movement ranged from 20° to 100°. This training exercise comprised a series of 10 movements to be performed in the presence of the visual sensory feedback, and then 10 movements in the presence of visual and vibratory sensory feedbacks and 10 movements with the vibration alone. During the performance of the movement, the subjects were requested to mark a pause time on the target to be achieved before starting again towards the other target. A sound notified the stable character of the position of the avatar when it had not moved for 500 ms. However, it did not notify the fact that the subjects were on the correct target. The target could therefore be validated only with vision and/or vibration. At the end of each test the trace of the movement was shown to the participants. This enabled them to judge the speed of performance of movement and of the precision over the whole of the test. The duration for performing the test was proportional to the amplitude of the back and forth movements to be performed and extended from approximately 20 seconds to 45 seconds for the test with 100° of amplitude. Once every 3 series of 10 movements had ended, the participants went on to the test phase. This exercise had an approximate duration of 45 minutes.

Test phase: The test phase comprised a total of 8 blocks each of 3 tests, with one test per type of sensory feedback. Every two blocks (i.e. every 6 movements) a test with no sensory feedback was implemented. This test served as the base line for evaluating the performances with the other types of sensory feedback. A total of 28 movements were then performed in this test phase. In a similar manner to the training phase, a pause time on the targets to be achieved was requested. The objective was not to make the most back and forth movements possible but to be precise and on the correct targets. At the end of the tests, the trace of the movement made was displayed on the screen to show the participants the quality of their performance. This test phase had an approximate duration of 40 minutes.

Results

Figure 3:
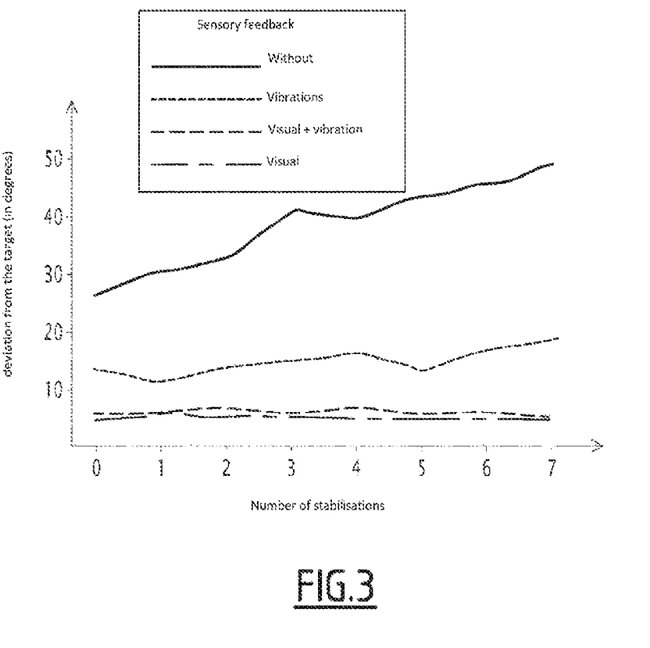
FIG. 3 is a graph showing the distribution of the deviations from the target for each movement during tests of back and forth movements between two targets by means of a virtual avatar for three types of sensory feedback and a configuration in the absence of any sensory feedback in non-amputated subjects.

FIG. 3 illustrates the behaviour of the non-amputated subjects and shows the distribution of the deviations from the target for each movement during back and forth tests shown for the four types of sensory feedback. The X-axis represents the number of stabilisations performed by the subjects during the back and forth movements. The Y-axis represents the deviation from this target. A back and forth movement is equivalent to two iterations. The solid or broken lines represent the mean of the deviations from the target for all the tests using the same type of sensory feedback.

The traces show that, for the sensory feedbacks including vision, the subjects remain on average very precise with a deviation of less than 10% for more than 3 back and forth movements. When the trace of the condition is looked at with the vibrotactile sensory feedback alone, this is stable over time with values superior to the traces including vision but below the limit of 20°, which corresponds to the discretisation of 2 vibrators. It is observed clearly that the last condition with no sensory feedback is different from the other 3 conditions with an error that increases over time. This attests to the fact that the subjects having no sensory feedback on the performance of their action lost their references and deviated from the targets over time. This trace therefore illustrates the possible effect of the vibrotactile sensory feedback in that it enables the subjects to locate themselves in space. The information transmitted by the vibrations is therefore correctly used and efficient.

The invention claimed is:

1. A method for controlling a limb of a virtual avatar by the myoelectric activities of a limb of a subject, comprising a first calibration step comprising:
acquiring first and second raw calibration myoelectric activity signals by a device for measuring myoelectric activity signals, the first and second raw calibration myoelectric activity signals resulting from contractions of variable intensities of first and second antagonistic muscles of the limb of the subject respectively, during a given period, and then:

determining the envelope of each of the first and second signals by a processing device, determining the minimum and maximum myoelectric activities from the envelope of each of the first and second signals by the processing device, then, for each of the two antagonistic muscles determining a myoelectric activity threshold by the processing device, normalizing the maximum myoelectric activity and the myoelectric activity threshold by the processing device, determining a coefficient of conversion of the normalized myoelectric activity into a component of speed of movement of a limb of the virtual avatar by the processing device, and the method for controlling comprising a second step of moving the limb of the virtual avatar comprising:

acquiring first and second raw myoelectric activity signal by the device for measuring myoelectric activity signals, the first and second raw myoelectric activity signals resulting from contractions of the two antagonistic muscles of the limb of the subject, during a given period, and then, for each of the first and second raw myoelectric activity signals:

normalizing the myoelectric activity resulting from the signal by the processing device, converting the normalized myoelectric activity into a component of speed of movement of a limb of a virtual avatar by applying the coefficient of conversion by the processing device, determining a speed and a direction of movement of the limb of the virtual avatar by subtracting the movement speed components obtained for each of the muscles by the processing device, and moving the limb of the virtual avatar with the speed and direction of movement determined by the processing device.

2. The method for controlling according to claim 1, wherein, simultaneously with the step of moving the limb of the virtual avatar with the determined speed and direction of movement, the method comprises the activation of a sensory feedback device disposed on the limb of the subject, the sensory feedback device being activated selectively and discretely according to predetermined ranges of values of a sensory parameter.

3. The method for controlling according to claim 2, wherein the sensory parameter is selected from a bending angle of an elbow of the virtual avatar, an anterior elevation angle of a shoulder of the virtual avatar an abduction/adduction angle of the shoulder of the virtual avatar, a medial or lateral rotation angle of the shoulder of the virtual avatar, a bending angle of a wrist of the virtual avatar, a radial or ulnar rotation angle of the virtual avatar, a degree of opening of a hand of the virtual avatar, a degree of opening of a finger grip involving the thumb and one or more other fingers of the hand of the virtual avatar, a gripping force of a hand of the virtual avatar, a bending angle of a knee of the virtual avatar, a bending angle of the ankle of the virtual avatar, a speed of rotation of one of the movements mentioned in the present list, or any other sensory modality able to be replaced by vibrations, such as the warmth or configuration of a myoelectric prosthesis of the subject.

4. The method for controlling according to claim 1, wherein the device for measuring myoelectric activity signals comprises a plurality of electrodes, the method comprising selecting two electrodes from the plurality of electrodes enabling a maximum acquisition of the myoelectric activity signals of each of the two antagonistic muscles.

5. The method for controlling according to claim 1, wherein determining the minimum and maximum myoelectric activities from the envelope of the signal comprises:

setting the raw calibration myoelectric activity signal to a zero mean value, determining the absolute value of the raw calibration myoelectric activity signal set to zero mean value, the signal in absolute value to obtain the envelope therefrom, and from the envelope of the filtered signal, determining the minimum value and the maximum value of the envelope of the filtered signal.

6. A system adapted for implementing the method for controlling a limb of a virtual avatar by the myoelectric activities of a limb of a subject according to claim 1, the system comprising:

a device for measuring myoelectric activity signals resulting from contractions of first and second antagonistic muscles of the limb of the subject, suitable for acquiring first and second raw calibration myoelectric activity signals resulting from contractions of variable intensities of first and second antagonistic muscles of the limb of the subject respectively, during a given period, and first and second raw myoelectric activity signals resulting from contractions of the two antagonistic muscles of the limb of the subject, during a given period, a processing device for processing the myoelectric activities comprising at least one display device configured for displaying the virtual avatar, the processing device being configured for, in a first calibration step, determining the envelope of each of the first and second signals, determining the minimum and maximum myoelectric activities the envelope of each of the first and second signals, determining a myoelectric activity threshold, normalizing the maximum myoelectric activity and the myoelectric activity threshold, determining a coefficient of conversion of the normalized myoelectric activity into a component of speed of movement of a limb of the virtual avatar, normalizing the myoelectric activity resulting from each of the first and second signals, converting the normalized myoelectric activity into a component of speed of movement of a limb of a virtual avatar by applying the coefficient of conversion, and in a second step of moving the limb of the virtual avatar for each of the first and second raw myoelectric activity signals:

normalizing the myoelectric activity resulting from the signal, converting the normalized myoelectric activity into a component of speed of movement of a limb of a virtual avatar by applying the coefficient of conversion, determining a speed and direction of movement of the limb of the virtual avatar by subtracting the movement speed components obtained for each of the muscles, and moving the limb of the virtual avatar with the determined speed and direction of movement.

7. The system according to claim 6, wherein the device for measuring comprises a plurality of electrodes and is in the form of a bracelet.

8. The system according to claim 6, furthermore comprising a sensory feedback device.

9. The system according to claim 8, wherein the sensory feedback device comprises a plurality of vibrating elements.

10. The system according to claim 8, wherein the processing device is configured for activating the sensory feedback device selectively and discretely according to predetermined ranges of values of a sensory parameter.

11. The system according to claim 6, wherein the device for measuring signals of myoelectric activity comprises a remote communication device configured for remotely communicating with the processing device.

* * * * *